US011264138B1

(12) United States Patent
Sughrue et al.

(10) Patent No.: US 11,264,138 B1
(45) Date of Patent: Mar. 1, 2022

(54) GENERATING BRAIN NETWORK IMPACT SCORES

(71) Applicant: Omniscient Neurotechnology Pty Limited, Sydney (AU)

(72) Inventors: Michael Edward Sughrue, Sydney (AU); Stephane Philippe Doyen, Glebe (AU); Peter James Nicholas, South Hurstville (AU); Bradley Allan Fernald, Saint Petersburg, FL (US)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/066,186

(22) Filed: Oct. 8, 2020

(51) Int. Cl.
*G16H 50/30* (2018.01)
*G16H 50/20* (2018.01)
(Continued)

(52) U.S. Cl.
CPC .............. *G16H 50/30* (2018.01); *A61B 5/055* (2013.01); *A61B 5/4088* (2013.01); *A61B 5/4848* (2013.01); *A61B 5/7264* (2013.01); *A61B 5/7275* (2013.01); *A61B 5/742* (2013.01); *G06F 16/9024* (2019.01); *G16H 40/20* (2018.01); *G16H 40/67* (2018.01); *G16H 50/20* (2018.01); *G16H 50/50* (2018.01); *G16H 50/70* (2018.01);
(Continued)

(58) Field of Classification Search
CPC ........ G16H 50/30; G16H 50/50; G16H 50/70; G16H 40/67; G16H 40/20; G16H 40/50; G16H 20/40; G16H 20/30; G16H 20/10; G16H 20/70; G06F 16/9024; A61B 5/055; A61B 5/4088; A61B 5/4848; A61B 5/7275; A61B 5/742; A61B 5/0022

USPC ......................................................... 705/2–3
See application file for complete search history.

(56) References Cited

U.S. PATENT DOCUMENTS 10,149,618 B1 * 12/2018 Tandon ................ A61B 5/0077
2011/0295515 A1 * 12/2011 Grady ................. A61B 5/4064
702/19

(Continued)

OTHER PUBLICATIONS

Du et al., "Structural brain network measures are superior to vascular burden scores in predicting early cognitive impairment in post stroke patients with small vessel disease" Neuroimage Clin., 2018,22:101712.

(Continued)

*Primary Examiner* — Michael Tomaszewski
(74) *Attorney, Agent, or Firm* — Fish & Richardson P.C.

(57) ABSTRACT

Methods, systems, and apparatus, including computer programs encoded on computer storage media, for generating a mental health prediction for a patient. One of the methods includes obtaining brain data captured by one or more sensors characterizing a brain of a patient; determining a network graph from the brain data, wherein: a node of the network graph corresponds to a parcellation in the brain of the patient, and a subset of nodes of the network graph corresponds to a particular functional area of the brain; generating, for each of a plurality of nodes in the network graph, a measure of centrality of the node; generating, for the particular functional area of the brain and using the generated measures of centrality, a health score representing a measure of health of the functional area of the brain; generating a mental health prediction for the patient using the health score.

21 Claims, 6 Drawing Sheets

(51) Int. Cl.

*G16H 50/70* (2018.01)
  *G16H 70/60* (2018.01)
  *G16H 50/50* (2018.01)
  *G16H 40/20* (2018.01)
  *G06F 16/901* (2019.01)
  *A61B 5/00* (2006.01)
  *A61B 5/055* (2006.01)
  *G16H 40/67* (2018.01)
  *G16H 20/10* (2018.01)
  *G16H 20/30* (2018.01)
  *G16H 20/40* (2018.01)
  *G16H 20/70* (2018.01)

(52) U.S. Cl.
  CPC ............ *G16H 70/60* (2018.01); *A61B 5/0022* (2013.01); *G16H 20/10* (2018.01); *G16H 20/30* (2018.01); *G16H 20/40* (2018.01); *G16H 20/70* (2018.01)

(56) References Cited

U.S. PATENT DOCUMENTS

| 2013/0231552 | A1* | 9/2013 | Grady | A61B 5/055 600/410 |
| 2015/0018664 | A1* | 1/2015 | Pereira | A61B 5/4064 600/410 |
| 2015/0164431 | A1* | 6/2015 | Terry | A61B 5/7264 600/408 |
| 2016/0300352 | A1* | 10/2016 | Raj | G06T 7/0012 |

OTHER PUBLICATIONS

Goubran et al., "Multimodal image registration and connectivity analysis for integration of connectomic data from microscopy to MRI" Nature Comm., Dec. 2019, 10(1):1-7.

medium.com [online], "A Simple Guide to Scikit-learn Pipelines", Feb. 2019, retrieved on Oct. 19, 2020, retrieved from URL <https://medium.com/vickdata/a-simple-guide-to-scikit-learn-pipelines-4acOd974bdcf>, 6 pages.

* cited by examiner

GENERATING BRAIN NETWORK IMPACT SCORES

CROSS-REFERENCE TO RELATED APPLICATIONS

This application is related to the U.S. patent application entitled "Centrality Rankings of Network Graphs Generated using Connectomic Brain Data," to Michael Edward Sughrue, Stephane Philippe Doyen, Peter James Nicholas, and Hugh Monro Taylor, filed on the same day as the present application and incorporated herein by reference in its entirety.

BACKGROUND

This specification relates to processing data related to the brain of a patient, e.g., functional magnetic resonance imaging (MM) data and/or tractography data.

Brain functional connectivity data characterizes, for each of one or more pairs of locations within the brain of a patient, the degree to which brain activity in the pair of locations is correlated.

One can process images of the brain of a patient, e.g., using magnetic resonance imaging (MM), diffusion tensor imaging (DTI), or functional MRI imaging (fMRI). Diffusion tensor imaging uses magnetic resonance images to measure diffusion of water in a human brain. One can use the measured diffusion to generate tractography data, which can include images of neural tracts and corresponding white matter fibers of the subject brain.

Data related to the brain of a single patient can be highly complex and high-dimensional, and therefore difficult for a clinician to manually inspect and parse, e.g., to plan a surgery or categorize the patient for follow up regarding a brain disease or mental disorder. For example, a correlation matrix, e.g., a correlation matrix of fMRI data, of the brain of a patient can be a matrix with hundreds of thousands or millions of elements.

SUMMARY

This specification describes a system that is configured to determine the health of one or more regions of the brain of a patient. As a particular example, the system can determine a health score that characterizes the health of a functional area of the brain of the patient, e.g., the language region of the brain. As another particular example, the system can determine a health score that characterizes the health of the entire brain of the patient.

The system can represent the brain of the patient as a network, e.g., a network represented by a network graph, where each node in the network graph corresponds to a respective sub-region of the brain and each edge between two nodes corresponding to respective sub-regions characterizes a connection between the two sub-regions. For example, each node in the graph can correspond to a parcellation of the brain, and each edge can correspond to one or more tracts of the brain connecting respective parcellations. The system can then determine a health score for a subset of the nodes of the network graph (e.g., a subset that includes each node corresponding to a parcellation that is in the language region of the brain) or for the entire network graph.

In some implementations, the health score corresponding to a subset of nodes can be a machine-learned score that is computed using one or more of i) the number of tracts corresponding to each node in the subset of nodes, ii) a measure of health of the tracts corresponding to each node in the subset of nodes, and iii) a measure of centrality of each node in the subset of nodes within the network graph. In some implementations, the measure of centrality of a node is the PageRank of the node within the network graph. In some implementations, the system determines the measure of health of the tracts using fractional anisotropy.

After the system generates the health score for a particular region of the brain, the system can use the health score to determine a mental health prediction for the patient. The mental health prediction can include a determination of whether to perform a particular treatment on the brain of the patient, e.g., whether to administer a particular drug, whether to perform transcranial magnetic stimulation (TMS), or whether to perform a particular surgery. Instead or in addition, the mental health prediction can include a prediction of whether the patient has a particular brain disease, e.g., autism, schizophrenia, or depression. Instead or in addition, the mental health prediction can include a determination of degree of trauma that the particular region of the brain has experienced. Instead or in addition, the mental health prediction can include a measure of change in the health of the brain of the patient over time, e.g., a difference between a first health score generated from brain data captured at a first time point and a second health score generated from brain data captured at a second time point. Instead or in addition, the mental health prediction can include a prediction of a relationship between two or more different regions of the brain, e.g., a degree of correlation between respective health scores of the different regions of the brain.

In this specification, brain data can be any data characterizing the brain of a patient. For example, brain data can include one or both of i) direct measurement data of the brain of the patient, e.g., images of the brain collected using brain imaging techniques, or ii) data that has been derived or generated from initial measurement data of the brain of the patient, e.g., correlation matrices.

Particular embodiments of the subject matter described in this specification can be implemented so as to realize one or more of the following advantages.

As discussed above, a set of brain data characterizing the brain of a single patient can often be incredibly large and complicated, and thus it can be difficult and time consuming for a user to extract useful information from the set of brain data. Using techniques described in this specification, a system can process brain data of a patient and automatically determine a current health of one or more regions in the brain, or of the entire brain. A user can then user the determined health scores to make clinical decisions about the treatment of the patient. Thus, the amount of time that a user must spend analyzing raw brain data to determine the health of the brain can be drastically reduced or even eliminated, resulting in improved outcomes for patients, users and/or clinicians, especially when effective care requires time sensitive investigations.

According to one or more embodiments described in this specification, users can use health scores corresponding to a particular region in the brain to standardize treatments across patients. As a particular example, medical professionals who are experts on a brain disease associated with the particular region of the brain can establish standards for care with reference to health score benchmarks, e.g., these professionals can provide a first treatment (e.g., TMS) to a patient if the health score of the patient is below a threshold and provide a second treatment (e.g., brain surgery) to the patient if the health score of the patient is above the threshold. As another particular example, organizers of a drug trial can use health scores of a patient across time to measure the efficacy of the drug and/or to determine eligibility for the trial, e.g., determining that the initial health score of the patient must be above a particular threshold to be eligible to participate in the trial.

Different users who work separately, e.g., clinicians at different hospitals or in different cities, can use the health scores described in this specification as a common interpretable measure of the health of patients. For example, two clinicians of the same patient who has experience brain trauma can use the health score of the affected region of the patient's brain to discuss the patient's injury in a way that both clinicians understand.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a system that can process brain data of a patient to determine the health of the brain of the patient.

Figure 1A:
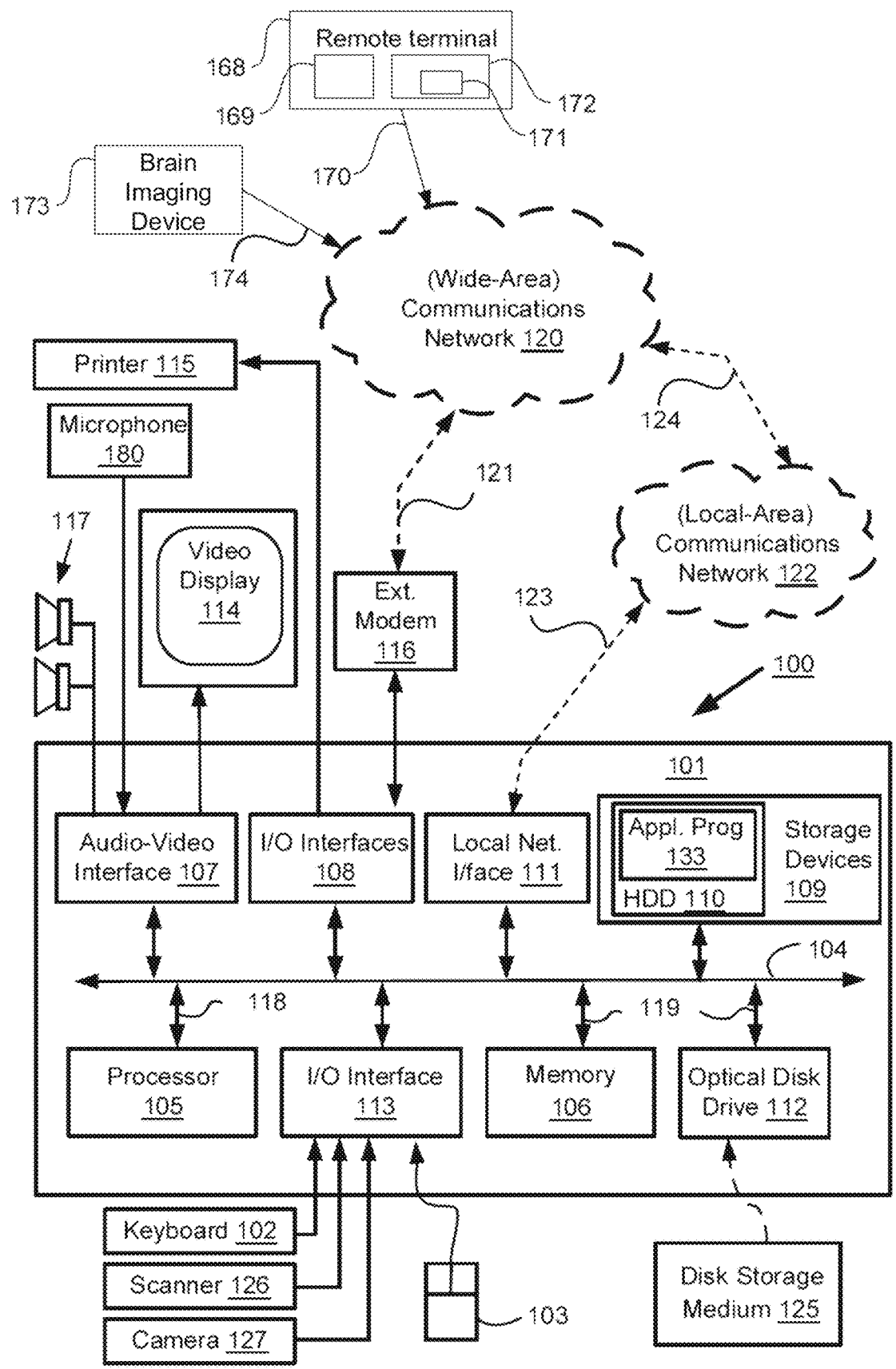
FIG. 1A and FIG. 1B are block diagrams that illustrate an example computer system for use in processing medical images.
Figure 1B:
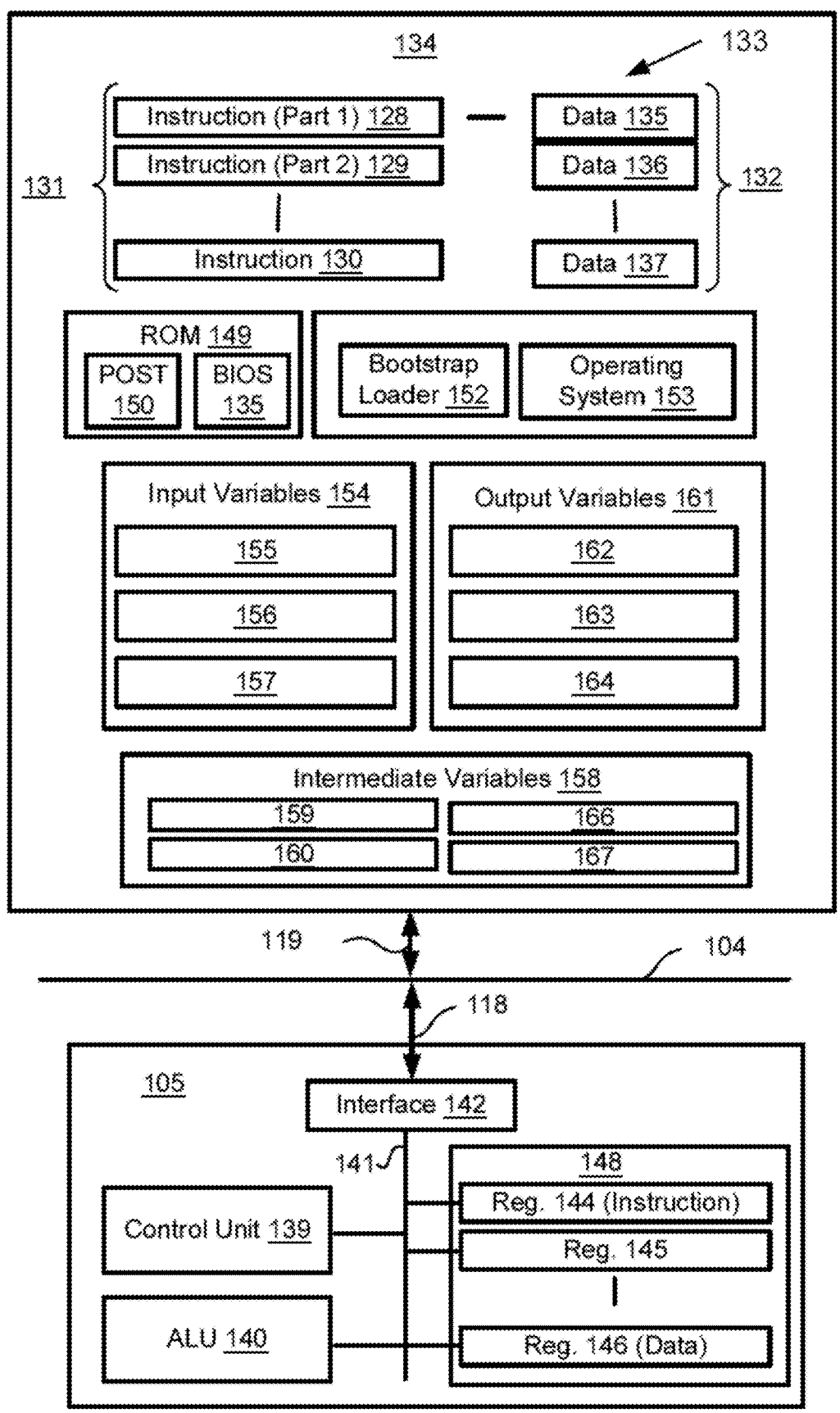

FIGS. 1A and 1B are block diagrams of a general-purpose computer system 100 upon which one can practice arrangements described in this specification. The following description is directed primarily to a computer server module 101. However, the description applies equally or equivalently to one or more remote terminals 168.

As seen in FIG. 1A, the computer system 100 includes: the server computer module 101; input devices such as a keyboard 102, a pointer device 103 (e.g., a mouse), a scanner 126, a camera 127, and a microphone 180; and output devices including a printer 115, a display device 114 and loudspeakers 117. An external Modulator-Demodulator (Modem) transceiver device 116 may be used by the computer server module 101 for communicating to and from the remote terminal 168 over a computer communications network 120 via a connection 121 and a connection 170. The aforementioned communication can take place between the remote terminal 168 and "the cloud" which in the present description comprises at least the one server module 101. The remote terminal 168 typically has input and output devices (not shown) which are similar to those described in regard to the server module 101. The communications network 120 may be a wide-area network (WAN), such as the Internet, a cellular telecommunications network, or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer server module 101 typically includes at least one processor unit 105, and a memory unit 106. For example, the memory unit 106 may have semiconductor random access memory (RAM) and semiconductor read only memory (ROM). The remote terminal 168 typically includes as least one processor 169 and a memory 172. The computer server module 101 also includes a number of input/output (I/O) interfaces including: an audio-video interface 107 that couples to the video display 114, loudspeakers 117 and microphone 180; an I/O interface 113 that couples to the keyboard 102, mouse 103, scanner 126, camera 127 and optionally a joystick or other human interface device (not illustrated); and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1A, the local communications network 122 may also couple to the wide network 120 via a connection 124, which would typically include a so-called "firewall" device or device of similar functionality. The local network interface 111 may include an Ethernet circuit card, a Bluetooth® wireless arrangement or an IEEE 802.11 wireless arrangement; however, numerous other types of interfaces may be practiced for the interface 111.

The I/O interfaces 108 and 113 may afford either or both of serial or parallel connectivity; the former may be implemented according to the Universal Serial Bus (USB) standards and having corresponding USB connectors (not illustrated). Storage memory devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119.

The techniques described in this specification may be implemented using the computer system 100, e.g., may be implemented as one or more software application programs 133 executable within the computer system 100. In some implementations, the one or more software application programs 133 execute on the computer server module 101 (the remote terminal 168 may also perform processing jointly with the computer server module 101), and a browser 171 executes on the processor 169 in the remote terminal, thereby enabling a user of the remote terminal 168 to access the software application programs 133 executing on the server 101 (which is often referred to as "the cloud") using the browser 171. In particular, the techniques described in this specification may be effected by instructions 131 (see FIG. 1B) in the software 133 that are carried out within the computer system 100. The software instructions 131 may be formed as one or more code modules, each for performing one or more particular tasks. The software may also be divided into two separate parts, in which a first part and the corresponding code modules performs the described techniques and a second part and the corresponding code modules manage a user interface between the first part and the user.

The software may be stored in a computer readable medium, including the storage devices described below, for example. The software is loaded into the computer system 100 from the computer readable medium, and then executed by the computer system 100. A computer readable medium having such software or computer program recorded on the computer readable medium is a computer program product. Software modules for that execute techniques described in this specification may also be distributed using a Web browser.

The software 133 is typically stored in the HDD 110 or the memory 106 (and possibly at least to some extent in the memory 172 of the remote terminal 168). The software is loaded into the computer system 100 from a computer readable medium, and executed by the computer system 100. Thus, for example, the software 133, which can include one or more programs, may be stored on an optically readable disk storage medium (e.g., CD-ROM) 125 that is read by the optical disk drive 112. A computer readable medium having such software or computer program recorded on it is a computer program product.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any non-transitory tangible storage medium that provides recorded instructions and/or data to the computer system 100 for execution and/or processing. Examples of such storage media include floppy disks, magnetic tape, CD-ROM, DVD, Blu-Ray™ Disc, a hard disk drive, a ROM or integrated circuit, USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. For example, through manipulation of the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1B is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1A.

When the computer module 101 is initially powered up, a power-on self-test (POST) program 150 can execute. The POST program 150 can be stored in a ROM 149 of the semiconductor memory 106 of FIG. 1A. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 can activate the hard disk drive 110 of FIG. 1A. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfil various high-level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1A must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1B, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119. The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively. Depending upon the relative size of the instructions 131 and the memory locations 128-130, a particular instruction may be stored in a single memory location as depicted by the instruction shown in the memory location 130. Alternately, an instruction may be segmented into a number of parts each of which is stored in a separate memory location, as depicted by the instruction segments shown in the memory locations 128 and 129.

In general, the processor 105 is given a set of instructions which are executed therein. The processor 105 waits for a subsequent input, to which the processor 105 reacts to by executing another set of instructions. Each input may be provided from one or more of a number of sources, including data generated by one or more of the input devices 102, 103, data received from an external source 173, e.g., a brain imaging device 173 such such as an Mill or DTI scanner, across one of the networks 120, 122, data retrieved from one of the storage devices 106, 109 or data retrieved from a storage medium 125 inserted into the corresponding reader 112, all depicted in FIG. 1A. The execution of a set of the instructions may in some cases result in output of data. Execution may also involve storing data or variables to the memory 134.

Some techniques described in this specification use input variables 154, e.g., data sets characterizing the brain of a patient, which are stored in the memory 134 in corresponding memory locations 155, 156, 157. The techniques can produce output variables 161, which are stored in the memory 134 in corresponding memory locations 162, 163, 164.

Intermediate variables 158 may be stored in memory locations 159, 160, 166 and 167.

Referring to the processor 105 of FIG. 1B, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle can include i) a fetch operation, which fetches or reads an instruction 131 from a memory location 128, 129, 130; ii) a decode operation in which the control unit 139 determines which instruction has been fetched; and iii) an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 132.

Each step or sub-process in the techniques described in this specification may be associated with one or more segments of the program 133 and is performed by the register section 144, 145, 146, the ALU 140, and the control unit 139 in the processor 105 working together to perform the fetch, decode, and execute cycles for every instruction in the instruction set for the noted segments of the program 133. Although a cloud-based platform has been described for practicing the techniques described in this specification, other platform configurations can also be used. Furthermore, other hardware/software configurations and distributions can also be used for practicing the techniques described in this specification.

Figure 2A:
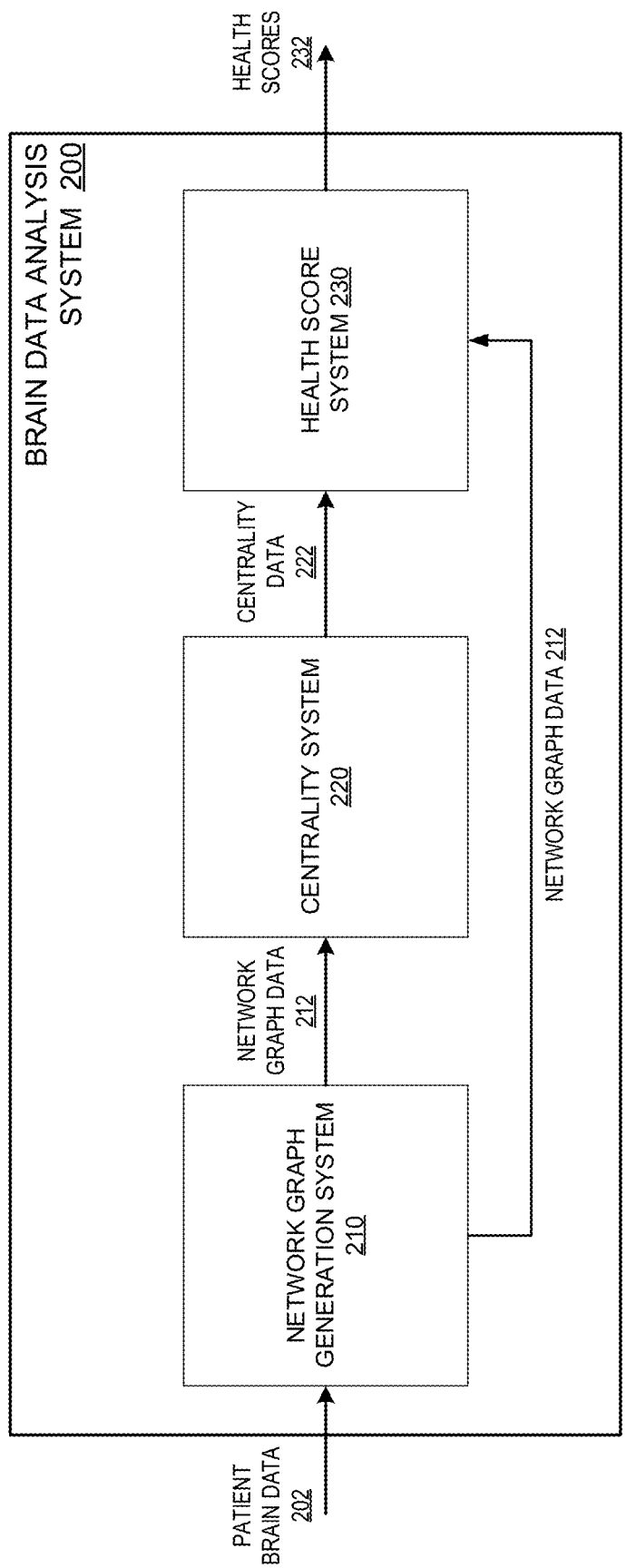
FIG. 2A is a diagram of an example brain data analysis system.

FIG. 2A is a diagram of an example brain data analysis system 200. The brain data analysis system 200 is an example of a system implemented as computer programs on one or more computers in one or more locations, in which the systems, components, and techniques described below can be implemented.

The brain data analysis system 100 is configured to obtain patient brain data 202 characterizing the brain of a patient and process the patient brain data 202 to generate one or more health scores 232 corresponding to respective regions of the brain of the patient. In some implementations, the patient brain data 202 includes brain tractography data that identifies, for each pair of two parcellations in a set of parcellations in the brain of the patient, a number of tracts connecting the two parcellations. In some such implementations, the tractography data can be normalized. For example, the number of tracks between each pair of parcellations can be normalized according to the largest number of tracts connecting a respective pair of parcellations in the brain of the patient, or according to the total number of tracts in the brain of the patient.

The set of parcellations can be defined by a brain atlas. In this specification, a brain atlas is data that defines one or more parcellations of a brain of a patient, e.g., by defining in a common three-dimensional coordinate system the coordinates of the outline of the parcellation or the volume of the parcellation.

Instead or in addition, the patient brain data 202 can include data characterizing a health of the tracts connecting respective pairs of parcellations in the brain of the patient. As a particular example, the patient brain data 202 can include fractional anisotropy data that characterizes, for each pair of parcellations in the brain of the patient that share at least one tract, a health of the tracts connecting the pair of parcellations. As another particular example, the patient brain data 202 can include correlation data that characterizes, for each pair of parcellations in the brain of the patient, a degree of correlation between the brain activity of the pair of parcellations. For instance, the patient brain data 202 can include a correlation matrix that includes a respective row and column for each parcellation, where the value of each element is the degree of correlation between the parcellation corresponding to the row and the parcellation corresponding to the column.

In some cases, the number of tracts in the brain of the patient identified in the brain data 202 can depend on the particular device used to capture the brain tractography data from the brain of the patient and/or the time or location at which the tractography data was captured. That is, in this specification "a number of tracts" refers to the number of tracts identified in a particular set of brain data 202 captured by a respective machine at a respective time point.

The network graph generation system 210 is configured to receive the patient brain data 202 and to generate network graph data 212 according to the patient brain data 202. The network graph data 212 defines a network graph that characterizes the brain of the patient. For example, each node in the network graph can correspond to a respective region of the brain of the patient, e.g., a respective parcellation.

Each edge between a pair of nodes in the network graph can characterize a connection between the pair of nodes. For example, the network graph can include an edge between a first node and a second node if there exists one or more tracts connecting the parcellation corresponding to the first node and the parcellation corresponding to the second node, according to the patient brain data 202. In some implementations, the edge between a first node and a second node can be weighted according to a number of tracts connecting the corresponding parcellations; that is, a higher edge weight indicates a larger number of tracts connecting the corresponding parcellations. Instead or in addition, the edge between a first node and a second node can be weighted according to the health of the tracts connecting the corresponding parcellations; that is, a higher edge weight indicates better health of the tracts connecting the corresponding parcellations.

Exemplary network graphs are described in more detail below with respect to FIG. 3.

In some implementations, the network graph data 212 can be defined by an adjacency matrix. For example, the adjacency matrix can include a respective row and a respective column for each node in the network graph, where the element in to a particular row and column defines the edge between the node corresponding to the row and the node corresponding to the column. If the network graph is an unweighted graph, the adjacency matrix can include elements that have value 0 or 1, where value 0 indicates that there is no edge between the corresponding nodes and value 1 indicates that there is an edge between the corresponding nodes. If the network graph is a weighted graph, the value of each element can define the weight of the edge between the corresponding nodes.

The brain data analysis system 200 includes a centrality system 220 that is configured to receive the network graph data 212 and to process the network graph data 212 to generate centrality data 222 that characterizes a respective measure of centrality for each node in the network graph. The measure of centrality of a node in the network graph characterizes a level of "importance" of the node within the network graph. Typically, a first node that has more edges and higher edge weights has a higher measure of centrality than a second node that has fewer edges and lower edge weights.

As particular examples, the centrality data 222 can include, for each node in the network graph defined by the network graph data 212, one or more of: a PageRank of the node, the degree of the node (which measures the number of edges incident to the node), the strength of the node (which measures the sum of the edges incident to the node), the betweenness of the node (which measures the number of shortest paths between respective pairs of nodes in the graph that pass through the node), or the closeness of the node (which measures the reciprocal of the sum of the lengths of the shortest paths between the node and each other node in the graph).

In some implementations, the measures of centrality of respective nodes in the network graph can be normalized. For example, the measures of centrality can be normalized within the patient, e.g., according to the largest measure of centrality in the network graph or according to the sum of all measures of centrality in the network graph. As another example, the measures of centrality can be normalized across subjects, e.g., using multiple network graphs corresponding to respective different patients.

In some implementations, the centrality data 222 can include a ranking of the nodes according to the measures of centrality. In this specification, the position of a node in the ranking of nodes by their measures of centrality is called the "centrality ranking" of the node. Using the centrality ranking of the nodes, instead or in addition to the raw measures of centrality of the nodes, to generate health scores 232 can be useful because centrality rankings can serve to normalize the total number of brain tracts across all patients. In other words, centrality rankings are less sensitive to variation in the number of brain tracts across subjects.

For example, a first patient may naturally have significantly more brain tracts than a second patient, e.g., 2×, 5×, or 10× more brain tracts, while the health of the respective brains of the patients is roughly the same. In these cases, using the raw measures of centrality of the nodes in the brain graphs (corresponding to parcellations in the brain) to generate health scores 232 may incorrectly indicate that the brain of the first patient is significantly healthier than the brain of the second patient. Using the centrality rankings of the nodes, which are usually largely consistent across patients, instead or in addition to the raw measures of centrality, can normalize the health scores 232 for differences in the raw number of tracts in the brains of patients.

As another example, typically as a patient grows older the number tracts in the brain of the patient decreases, while the centrality rankings of the parcellations in the brain of the patient remain roughly the same. If the brain of the aging patient is otherwise healthy, then a user of the brain data analysis system 200 might prefer that the health scores 232 of respective regions of the brain of the patient not indicate that the brain of the patient is unhealthy. Thus, using centrality rankings can cause the health scores 232 of a patient to vary less as the patient ages just based on typical age-related reduction in the number of tracts not related to brain disease.

Conversely, some brain diseases, e.g., Alzheimer's or dementia, can cause particular parcellations to decay more quickly than other parcellations. In these cases, both the raw measures of centrality and the centrality rankings of the nodes corresponding to the particular parcellations affected by the disease will decrease as the disease progresses. Thus, the health scores 232 will correctly indicate an issue in the one or more regions of the brain that include the particular parcellations.

The brain data analysis system 200 includes a health score system 230 that is configured to receive i) the network graph data 212 from the network graph generation system 210 and ii) the centrality data 222 from the centrality system 220, and to generate the health scores 232.

The health score system 230 processes the network graph data 212 and the centrality data 222 using one or more machine learning models to generate a respective health score 232 for each of one or more regions of the brain. For example, the health score system 230 can generate a respective health score 232 for each of one or more functional areas of the brain, e.g., the visual region of the brain, the auditory region of the brain, the language region of the brain, the motor function region of the brain, etc. As another example, the health score system 230 can generate a health score 232 for the entire brain of the patient.

In some implementations, the machine learning models used by the health score system 230 are configured to generate health scores corresponding to a particular region of the brain. In some other implementations, the machine learning models are configured to generate heath scores corresponding to any region of the brain. That is, the region of the brain can be an input to the machine learning models. In yet another example, the system 230 can generate scores for both i) one or more functional areas of the brain and ii) the whole brain.

A training system for training an example machine learning model configured to generate health scores 232 is described below with respect to FIG. 2B.

The health score 232 corresponding to a region in the brain of the patient can be a single scalar value, e.g., a value between 0 and 1, characterizing the health of the region of the brain.

For example, the health score system 230 can compute a machine-learned linear or non-linear combination of one or more parameters of the network graph data 212 and/or the centrality data 222 to generate the health scores.

As a particular example, to generate the health score for a particular region of the brain of the patient, the health score system 230 can compute a machine-learned linear combination of i) the number of tracts incident to each parcellation in the particular region of the brain, ii) a measure of health of the tracts incident to each parcellation in the particular region of the brain, and iii) the measure of centrality of each node corresponding to a parcellation in the particular region of the brain. That is, for each node corresponding to a parcellation in the particular region of the brain, the linear model can include three machine-learned weights corresponding to the number of tracts of the parcellation, the health of the tracts of the parcellation, and the measure of centrality of the parcellation. Thus, the linear model includes 3N machine-learned weights, where N is the number of parcellations in the particular region of the brain. For example, the region of the brain can have 10, 24, 50, 100, or several hundred parcellations.

As another particular example, to generate the health score for a particular region of the brain of the patient, the health score system 230 can compute a machine-learned linear combination of i) the number of tracts connecting each pair of parcellations in the particular region of the brain, ii) a measure of health of the tracts connecting each pair of parcellations in the particular region of the brain, and iii) the measure of centrality of each node corresponding to a parcellation in the particular region of the brain. That is, the linear model can include ~$2N^2+N$ machine-learned weights, where N is the number of parcellations in the particular region of the brain As another particular example, to generate the health score for a particular region of the brain of the patient, the health score system 230 can compute a machine-learned linear combination of i) the number of tracts connecting each parcellation in the particular region with each other parcellation in the entire brain, ii) a measure of health of the tracts connecting each parcellation in the particular region with each other parcellation in the entire brain, and iii) the measure of centrality of each node corresponding to a parcellation in the particular region of the brain. That is, the linear model can include ~2NM+N machine-learned weights, where N is the number of parcellations in the particular region of the brain and M is the number of parcellations in the entire brain.

As another particular example, to generate the health score for a particular region of the brain of the patient, the health score system 230 can compute a machine-learned linear combination that includes one or more of: the centrality ranking of each node corresponding to a parcellation in the particular region, the edge weight of each edge incident to a node that represents a parcellation in the particular region, or a measure of correlation between the brain activity of each pair of parcellations in the particular region.

As another particular example, the machine-learned linear combination can include one or more higher-order terms of respective parameters in the network graph data 212 or the centrality data 222. For example, the machine-learned linear combination can include a weighted term, for each parcellation in the particular region, for the squared or cubed value of the number of tracts incident to the parcellation. As another example, the machine-learned linear combination can include a weighted term, for each parcellation in the particular region, for the squared or cubed value of the measure of centrality of the node in the network graph corresponding to the parcellation. As another example, the machine-learned linear combination can include a weighted term, for each parcellation in the particular region, for the squared or cubed value of the measure of health of the tracts incident to the parcellation.

In some implementations, during training, a training system can optimize the linear function using regularization, e.g., L2 regularization.

As another example, the health score system 230 can generate health scores using tree-based regression models, e.g., one or more decision trees and/or one or more random forests.

Figure 2B:
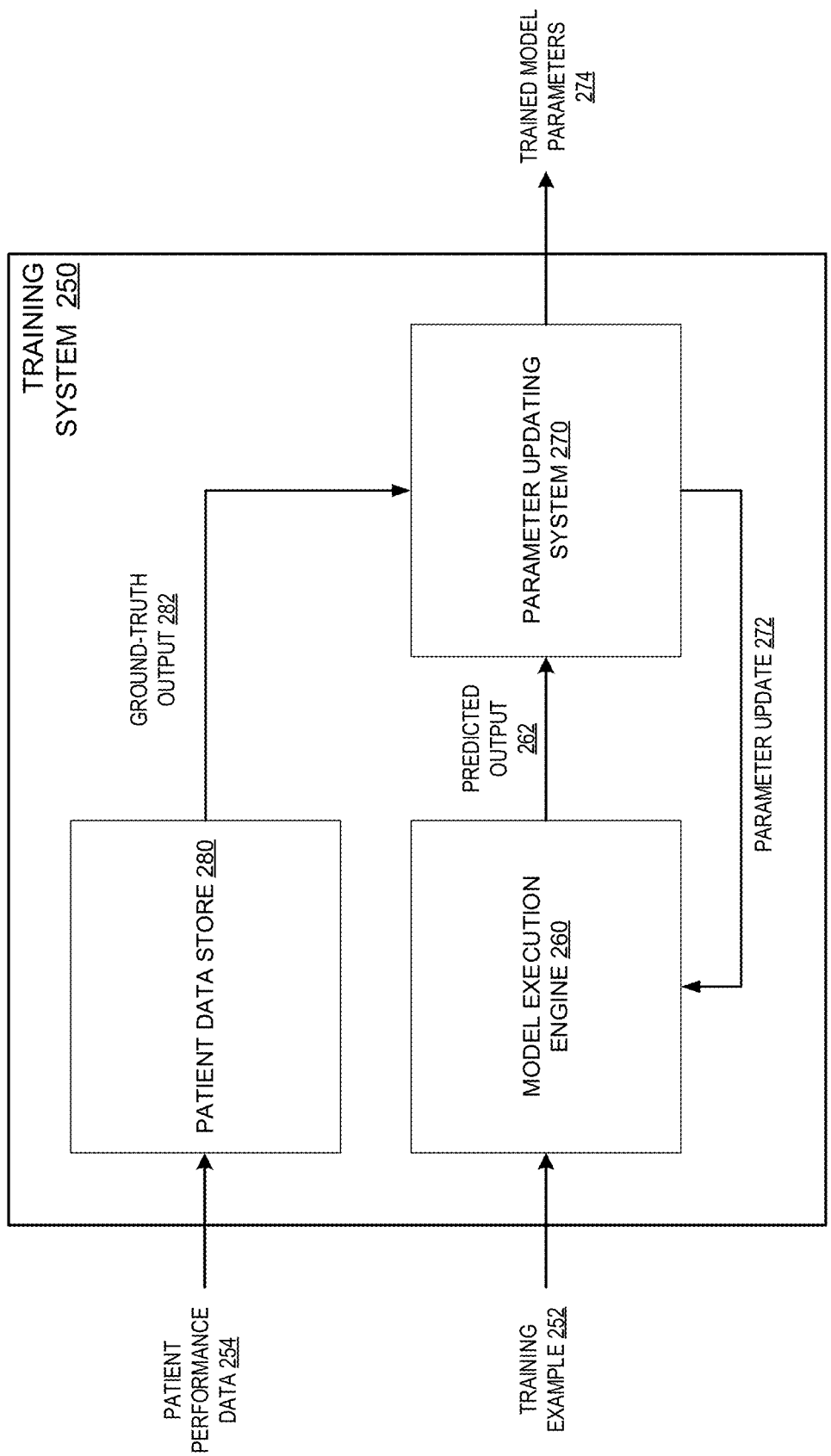
FIG. 2B is a diagram of an example training system.

FIG. 2B is a diagram of an example training system 250 for training a machine learning model to generate health scores, e.g., a machine learning model that is a component of the health score system 230 depicted in FIG. 2A. The training system 250 is an example of a system implemented as computer programs on one or more computers in one or more locations, in which the systems, components, and techniques described below can be implemented.

The training system 250 is configured to obtain multiple training examples 252 and to process the training examples 252 to generate trained model parameters 274 for the machine learning model. Each training example 252 includes a model input that the machine learning model is configured to receive corresponding to a respective patient. For example, if the machine learning model is configured to generate a health score for a region of the brain of a patient by computing a linear combination of multiple terms (e.g., the number/health of tracts incident to parcellations in the region, the measures of centrality and/or centrality rankings of nodes in a network graph corresponding to parcellations in the region, squared or cubed terms thereof, etc.), then each training example 252 can include the multiple terms measured in the brain of a respective patient.

The training system 250 includes a model execution engine 260 that is configured to process the training examples 252 using the machine learning model to generate predicted outputs 262 according to current values of the parameters of the machine learning model, e.g., current values of the weights of a linear model.

The training system 250 includes a parameter updating system 270 that is configured to obtain the predicted outputs 262 of the machine learning model and to generate a parameter update 272 for the parameters of the machine learning model according to an error in the predicted output 262. This error can be calculated based on an external measure of the health of the functional network in question, e.g., the error can be calculated based on a score of an individual linguistic ability when measuring the health of the linguistic network.

In some implementations, the training system 250 can train the machine learning model in a supervised fashion. For example, the parameter updating system 270 can compute the error in the predicted outputs 262 of the machine learning model using ground-truth outputs 282 corresponding to the training example 252, obtained from a patient data store 280. That is, each ground-truth output 282 is the output that the machine learning model should have generated in response to processing a respective training example 252. The parameter updating system 270 can determine a difference between the ground-truth outputs 282 and the predicted outputs 262, and determine an update to the parameters of the machine learning model according to the difference. As a particular example, if the machine learning model is a linear model, the parameter updating system 270 can generate the parameter update 272 using LASSO or ridge regression.

In some such implementations, the ground-truth outputs 282 are generated from clinical variables characterizing the performance of the respective patient in a clinical test. That is, the patient data store 280 can receive patient performance data 254 characterizing the performance of each patient in the clinical test, and determine the ground-truth health scores according to the patient performance data 254. The patient performance data 254 can include data corresponding to both patients who have a particular brain disease and patients who do not have any brain disease.

For example, if the machine learning model is configured to generate health scores characterizing the health of the language region of the brain, the patient can complete a language test to generate the ground-truth health scores, and brain data of the patient can be captured to generate the corresponding training example 252. As another example, if the machine learning model is configured to generate health scores characterizing the sensor-motor region of the brain, the patient can complete a movement test to generate ground-truth health scores, and brain data of the patient can be captured to generate the corresponding training example 252.

As a particular example, a patient might complete a clinical test measuring their proficiency in different language abilities before a brain surgery is performed on the language region of the brain of the patient. Also before the surgery, a system can capture brain data characterizing the language region of the brain. After the surgery, the patient can again take the same clinical test, and the system can again capture brain data of the language region of the brain. The training system 250 can then use the corresponding training examples and ground-truth outputs to train the machine learning model to quantify the degree of decay of the language region of the brain caused by the brain surgery.

As another particular example, the patient performance data 254 can include behavioral data of the patient. For example, after a treatment is provided to a particular region of the brain of the patient, e.g., a surgery or drug therapy, a system can capture brain data characterizing the particular region of the brain. The patient can then be externally observed and data characterizing their behavior recorded. The training system 250 can then generate ground-truth outputs 282 according to the behavioral data.

In some implementations, the parameter updating system 270 generates a parameter update 272 after each predicted output 262 is generated by the machine learning model. In some other implementations, the parameter updating system 270 generates a parameter update 272 after a batch of multiple predicted outputs 262 have been generated by the machine learning model.

After the final round of training, the training system 250 can output the final trained model parameters 274. For example, the training system 250 might determine to complete training after a predetermined number of training rounds, or after a marginal improvement in the performance of the machine learning model drops below a predetermined threshold level.

Figure 3:
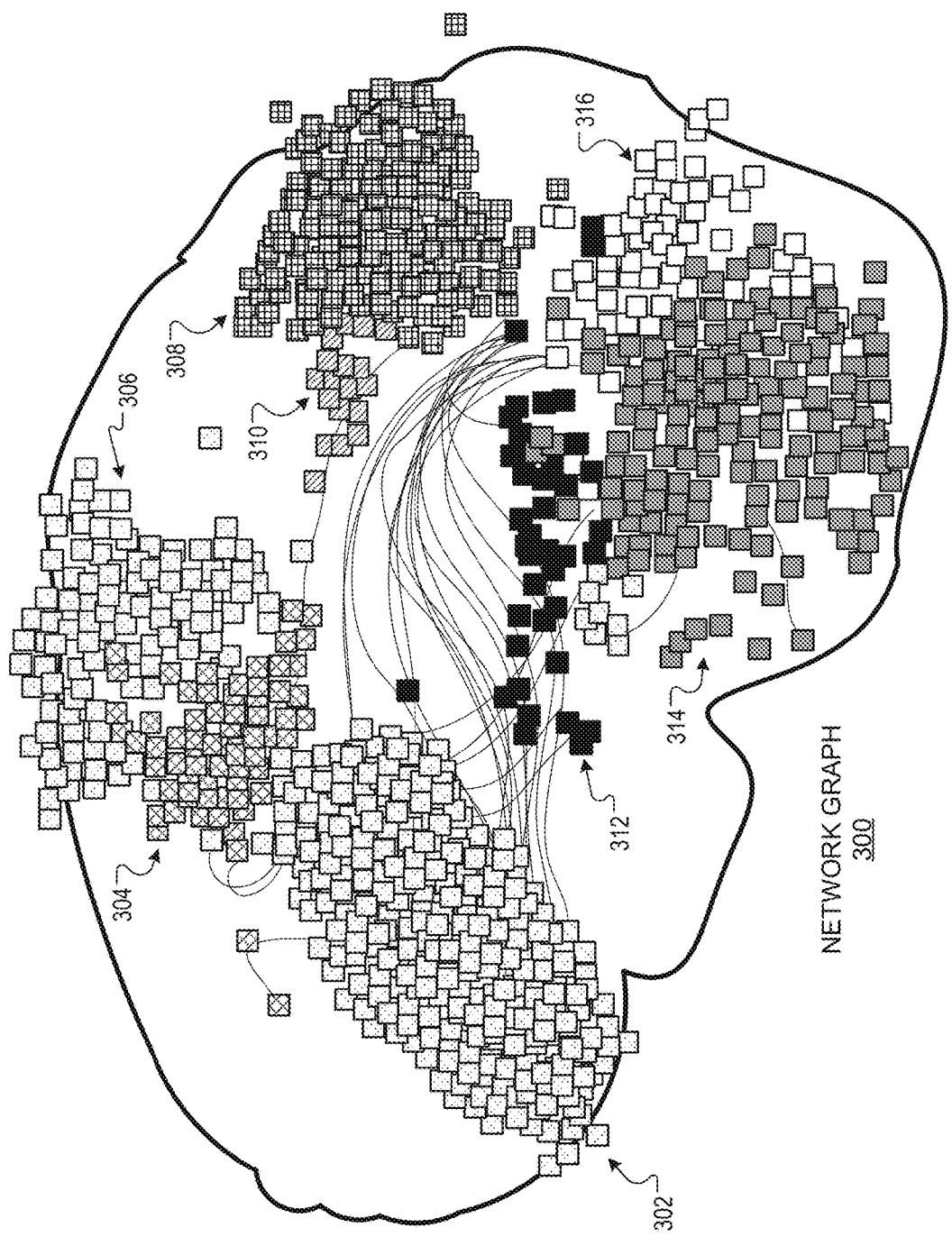
FIG. 3 illustrates a network graph characterizing the brain of a patient.

FIG. 3 illustrates an example network graph characterizing the brain of a patient.

Each node of the network graph corresponds to a respective parcellation in the brain of the patient. Each edge between a first node and a second node of the network graph corresponds to one or more brain tracts connecting the parcellation corresponding to the first node and the parcellation corresponding to the second node. Note that nodes and edges depicted in FIG. 3 are for illustrative purposes only; in reality, a network graph characterizing the brain of a patient can include many more nodes and edges, in many different configurations.

Generally, the edges of the network graph 300 are bidirectional; that is, the network graphs 300 is an undirected graph.

The network graph 300 includes eight subgraphs 302, 304, 306, 308, 310, 312, 314, and 316, depicted by respective different patterns. Each subgraph 302-316 corresponds to a respective functional area of the brain, and includes multiple parcellations. A health score system, e.g., the health score system 230 depicted in FIG. 2A, might generate a health score characterizing the health of one or more of the functional areas characterized by respective subgraphs 302-316 of the network graph 300. For example, the health score system might generate the health score for a particular subgraph 302-316 using one or more of: a number or weight of edges incident to the nodes of the subgraph, a measure of centrality of nodes of the subgraph, or a centrality ranking of nodes of the subgraph.

In some implementations, the weights of the edges between respective nodes of the graph 300 are machine-learned. For example, the weights of the edges of the graph 300 can be learned concurrently with the weights of the machine learning models of the health score system. As a particular example, a training system, e.g., the training system 250 depicted in FIG. 2B, might concurrently determine parameter updates to the weights of the edges of the graph 300 and the parameters of the machine learning model, using the same ground-truth outputs of the machine learning model.

As a particular example, the weight for an edge between a first node and a second node can be a learned function of one or more of i) the number of tracts connecting the parcellation corresponding to the first node and the parcellation corresponding to the second node, or ii) a health of the tracts connecting the parcellation corresponding to the first node and the parcellation corresponding to the second node, e.g., according to fractional anisotropy data. For example, the weights can be a linear combination of those two parameters; instead of in addition, the learned function can include a squared or cubed term corresponding to those two parameters.

In some implementations, the weights are the same for each edge in a respective subgraph 302-316 of the network graph 300. In some other implementations, the weights for each edge in each respective subgraph 302-316 of the network graph 300 are different.

Figure 4:
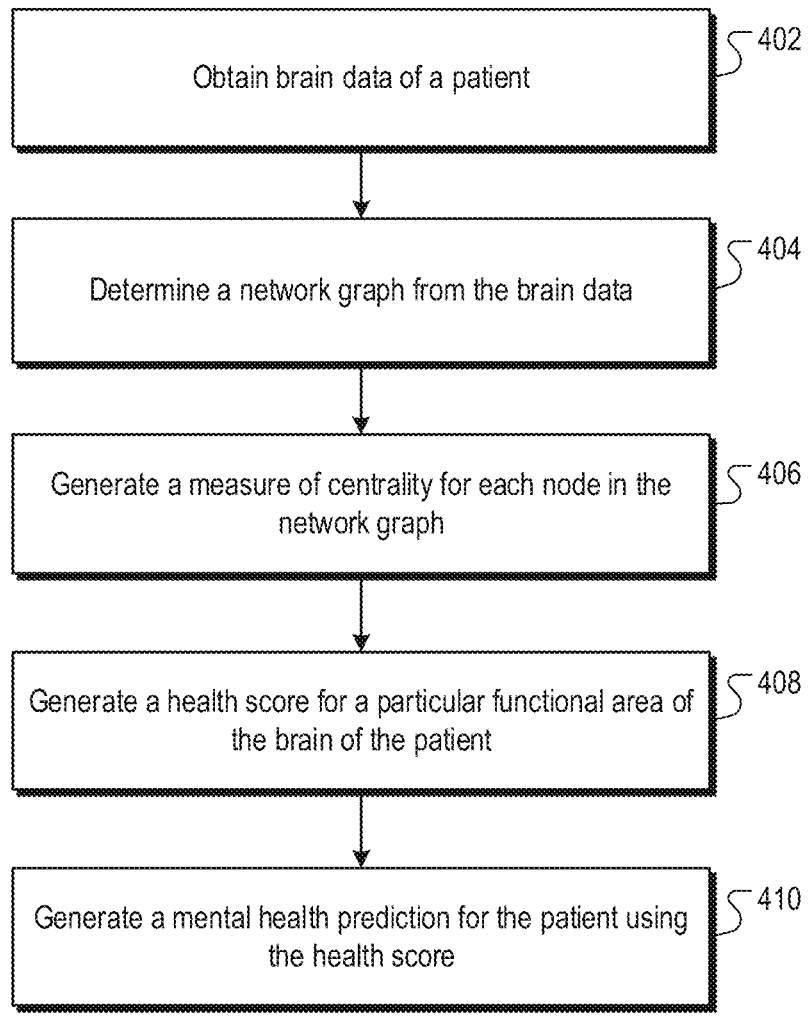
FIG. 4 is a flowchart of an example process for generating a health score characterizing the health of a region of the brain of a patient.

FIG. 4 is a flowchart of an example process 400 for generating a health score characterizing the health of a particular region of the brain of a patient. The process 400 can be implemented by one or more computer programs installed on one or more computers and programmed in accordance with this specification. For example, the process 400 can be performed by the computer server module depicted in FIG. 1A. For convenience, the process 400 will be described as being performed by a system of one or more computers.

The system obtains brain data of the patient (step 402). The brain data can be captured by one or more sensors. The brain data can include, for each of multiple pairs of parcellations formed from a set of parcellations where each pair includes a first parcellation and a second parcellation, data characterizing the number of tracts connecting the first parcellation and the second parcellation.

The system determines a network graph from the brain data of the patient (step 404). One or more nodes of the network graph can correspond to a parcellation in the brain of the patient. A subset of the nodes can correspond to the particular region of the brain of the patient, e.g., a particular functional area such as can be determined by a brain atlas (e.g., the MNI atlas). One or more edges between a first node and a second node of the network graph can characterize a connection between the parcellation corresponding to the first node and the parcellation corresponding to the second node.

In some implementations, the system generates an edge weight for each edge in the network graph. For example, the system can generate the edge weight according to the number of tracts between the parcellations corresponding to the respective nodes and/or a measure of health of the tracts between the parcellations corresponding to the respective nodes. For example, the edge weight can be a learned linear combination of the number of tracts and the measure of health of the tracts.

The system generates a measure of centrality for each node in the network graph (step 406). For example, the system can determine the PageRank of each node in the network graph. In some implementations, the system only generates a measure of centrality for nodes in the network graph that correspond to parcellations that are in the particular region of the brain.

The system generates a health score for the particular region of the brain using the generated measures of centrality (step 408). The health score represents a measure of health of the particular region of the brain. In some implementations, the system generates the health score according to i) the generated measures of centrality, ii) the number of tracts connecting each pair of parcellations in the particular region of the brain, and iii) a measure of health of the tracts connecting each pair of parcellations in the particular region of the brain. For example, the health score can be a machine-learned linear combination of the measures of centrality, the number of tracts of the pairs of parcellations, and the measures of health of the tracts of the pairs of parcellations.

In some implementations, generating a health score for the particular region of the brain can require extensive computation, e.g., when there are hundreds, thousands, or millions of machine-learned parameters to compute. As a particular example, the process 400 can take multiple hours for a computer system to perform.

The system generates a mental health prediction for the patient using the generated health score (step 410).

The mental health prediction can include a recommendation to consider performing a particular treatment for the brain of the patient. For example, the particular treatment can be associated with a range of health scores of the particular region of the brain. That is, the system can use previous clinical outcomes and corresponding health scores to determine the range of health scores. The range of health scores defines health scores that patients have had when the patients have achieved most clinical success with the particular treatment. For example, the system can use a machine learning model that has been trained using training examples corresponding to respective patients with specified clinical outcomes to determine the range of health scores.

As a particular example, a patient might have a tumor in the particular region of the brain, and a clinician may be attempting to select a treatment plan. Using the health score of the particular region, the clinician can better determine whether or not the particular region would react well to surgery. For example, the health score might be too low, indicating that the particular region is already significantly deteriorated. In this cases surgery might be too dangerous to the particular region of the brain, or the particular region of the brain might be unsalvageable making surgery unnecessary risk to the patient. The thresholds of the health scores for determining whether to perform surgery can be determined over time using the data and clinical outcomes of multiple different patients.

Instead or in addition, the mental health prediction can include a prediction of whether the patient has a particular brain disease. For example, the brain disease can be associated with a range of health scores of the particular region of the brain. That is, the system can use previous diagnoses and corresponding health scores to determine the range of health scores. That range of health scores defines health scores of a group of patients who have the particular brain disease. For example, the system can use a machine learning model that has been trained using training examples corresponding to respective patients to determine the range of health scores.

As a particular example, Alzheimer's often causes the brain to atrophy asymmetrically, i.e., some regions of the brain atrophy more quickly than others. For example, the "default mode" network of the brain is known to atrophy quickly in Alzheimer's patients. Using the process 400, the system can generate a health score for the default mode network for a patient that has been diagnosed with Alzheimer's, in order to determine the stage of the disease. The system can also generate a health score for the default mode network for a patient that is suspected as having Alzheimer's, in order to diagnose the disease. In either case, the thresholds of the health scores for determining the stage of the disease can be determined over time using the data and clinical outcomes of multiple different patients Instead or in addition, the mental health prediction can include a prediction of how the brain of the patient is changing over time. For example, the system can generate multiple health scores corresponding to respective time points using the process 400, and determine a change between the respective health scores.

For example, the system can generate a respective health score for the particular region of the brain of the patient before and after a treatment of the particular region of the brain of the patient. The treatment can include one or more of: a drug therapy, radiation therapy, magnetic therapy (e.g., TMS), light therapy (e.g., laser ablation), ultrasonic therapy (e.g., ablation), gene-modifying therapy, a surgery, physical therapy, yoga, or mental exercises, e.g., mental games or puzzles.

As a particular example, the mental health prediction can include a measure of efficacy of the treatment that was administered to the brain of the patient. That is, the system can i) process brain data captured before the treatment to generate a first health score and ii) process brain data captured after the treatment to generate a second health score. The system can then determine, according to the respective health scores, how effective the treatment was. Instead or in addition, the mental health prediction can include a performance measure for one or more entities that administered the treatment. That is, the system can determine, according to the respective health scores, how well the one or more entities administered the treatment. For example, the one or more entities can include one or more clinicians and/or one or more medical devices.

Instead or in addition, the mental health prediction can include a plan to administer a sequence of one or more treatments to the patient. For example, the system can determine (e.g., automatically or with the approval of a clinician) to administer a first treatment until a first benchmark is achieved, a second treatment until a second benchmark is achieved, etc. Each benchmark can correspond to a particular health score for the region of the brain. That is, during the sequence of treatments the system can iteratively generate health scores using the process 400, and whenever a benchmark is achieved the system can instruct a change to, or recommend that a user change, the treatment of the patient.

Instead or in addition, the mental health prediction can include a prediction of a relationship between different regions of the brain over time. For example, the system can use the process 400 to determine a respective health score for two different regions of the brain of the patient at a first time point, and then determine a respective health score for the two different regions of the brain of the patient at a second, later time point. The system can then determine how the first region is changing in relation to how the second region is changing. The system can use this information, e.g., to recommend treatment and/or follow-up for the patient and/or categorize the patient.

In some implementations, the system can perform the process 400 continuously in real-time. That is, the system can iteratively obtain new brain data of a patient and process the brain data to generate a new mental health prediction for the patient.

As a particular example, while a patient is undergoing brain surgery, the system can continuously capture brain data of the patient (e.g., using intraoperative MM), and process the brain data to determine if further resection is feasible without causing neurological deficit.

As another particular example, a clinician or the system can apply an electrical current to a particular region of the brain of a patient through an implantable stimulator and determine one or more changes in the health scores of the particular region of the brain across time. For example, the system can generate a mental health prediction, using a change in the health scores of the particular region of the brain, that indicates whether the electrical current is being properly placed and/or whether the parameters are properly designed. The mental health prediction can also identify how the placement of the electrical current and/or the parameters of the electrical current might be adjusted.

As another particular example, before administering a therapy to a patient (e.g., before administering a drug), a clinician can perform subtherapeutic tests of the therapy, where the therapy is delivered at a lower rate than is typically deemed therapeutic. The system can receive brain data of the patient that was captured during or after the subtherapeutic tests, and process the brain data to generate a mental health prediction that includes a prediction of the efficacy of the therapy, prior to the administration of the therapy. Instead or in addition, the mental health prediction can identify one or more side effects of the therapy, prior to the administration of the therapy.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g, a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

In addition to the embodiments described above, the following embodiments are also innovative:

Embodiment 1 is a method comprising:
obtaining brain data captured by one or more sensors characterizing a brain of a patient, wherein the brain data comprises, for each of a plurality of pairs of parcellations formed from a set of parcellations where each pair comprises a first parcellation and a second parcellation, data characterizing a number of tracts connecting the first parcellation and the second parcellation;

determining a network graph from the brain data, wherein:
    a node of the network graph corresponds to a parcellation in the brain of the patient, and
    a subset of nodes of the network graph corresponds to a particular functional area of the brain;

generating, for each of a plurality of nodes in the network graph, a measure of centrality of the node;

generating, for the particular functional area of the brain and using the generated measures of centrality, a health score representing a measure of health of the functional area of the brain; and generating a mental health prediction for the patient using the health score.

Embodiment 2 is the method of embodiment 1, wherein:
an edge between a first node and a second node of the network graph characterizes a connection between the parcellation corresponding to the first node and the parcellation corresponding to the second node, and determining a network graph from the brain data comprises, for an edge between a first node and a second node of the network graph, generating an edge weight according to the number of tracts connecting the parcellation corresponding to the first node and the parcellation corresponding to the second node;

Embodiment 3 is the method of any one of embodiments 1 or 2, wherein the edge weight for the edge between a first node and a second node in the network graph is generated according to i) the number of tracts connecting the parcellation corresponding to the first node and the parcellation corresponding to the second node and ii) a measure of health of the tracts connecting the parcellation corresponding to the first node and the parcellation corresponding to the second node.

Embodiment 4 is the method of embodiment 3, wherein the edge weight for the edge between the first node and the second node is a machine-learned linear combination of i) the number of tracts connecting the parcellation corresponding to the first node and the parcellation corresponding to the second node and ii) a measure of health of the tracts connecting the parcellation corresponding to the first node and the parcellation corresponding to the second node.

Embodiment 5 is the method of any one of embodiments 1-4, further comprising generating, for each of a plurality of subsets of nodes of the network graph wherein each subset corresponds to a different functional area of the brain and using the generated measures of centrality, a respective health score representing a measure of health of the respective functional areas of the brain.

Embodiment 6 is the method of embodiment 5, wherein generating a mental health prediction for the patient comprises determining a relationship between the measures of health of a plurality of different functional areas of the brain.

Embodiment 7 is the method of any one of embodiments 1-6, wherein generating a health score for a subset of parcellations comprises generating the health score using i) the generated measures of centrality, ii) the number of tracts connecting each pair of parcellations in the subset of parcellations, and iii) a measure of health of the tracts connecting each pair of parcellations in the subset of parcellations.

Embodiment 8 is the method of embodiment 7, wherein the health score for a subset of parcellations is a machine-learned linear combination of i) the generated measures of centrality, ii) the number of tracts connecting each pair of parcellations in the subset of parcellations, and iii) a measure of health of the tracts connecting each pair of parcellations in the subset of parcellations.

Embodiment 9 is the method of any one of embodiments 1-8, wherein generating a mental health prediction for the patient comprises determining whether to perform a particular treatment on the brain of the patient.

Embodiment 10 is the method of embodiment 9, wherein the particular treatment is associated with a range of possible health of scores of the subset of parcellations.

Embodiment 11 is the method of embodiment 10, wherein the range of possible health scores associated with the particular treatment is machine learned, the learning comprising processing a plurality of training examples corresponding to respective other patients.

Embodiment 12 is the method of any one of embodiments 1-11, wherein generating a mental health prediction for the patient comprises generating a prediction of whether the patient has a particular brain disease.

Embodiment 13 is the method of embodiment 12, wherein the particular brain disease is associated with a range of possible health of scores of the subset of parcellations.

Embodiment 14 is the method of embodiment 13, wherein the range of possible health scores associated with the particular brain disease is machine learned, the learning comprising processing a plurality of training examples corresponding to respective other patients.

Embodiment 15 is the method of any one of embodiments 1-14, wherein:
the obtained brain data corresponds to a first time point;
the health score is a first health score that represents a measure of health of the functional area of the brain at the first time point;
the method further comprises:
obtaining second brain data corresponding to a second time point, and
generating, for the particular functional area of the brain, a second health score representing a measure of health of the functional area of the brain at the second time point; and
generating a mental health prediction for the patient comprises determining a change between the first health score and the second health score.

Embodiment 16 is the method of embodiment 15, wherein:
the first time point is a time point before a treatment, and
the second time point is a time point after the treatment.

Embodiment 17 is the method of embodiment 16, wherein the treatment comprises one or more of:
a drug therapy;
radiation therapy;
magnetic therapy;
light therapy;
ultrasonic therapy;
gene-modifying therapy;
a surgery;
physical therapy; or mental exercises.

Embodiment 18 is the method of any one of embodiments 16 or 17, wherein the mental health prediction comprises one or more of:
a measure of efficacy of the treatment; or
a performance measure of one or more entities that administered the treatment.

Embodiment 19 is the method of any one of embodiments 1-18, wherein generating a mental health prediction comprises generating a sequence of treatments, wherein each treatment in the sequence of treatments corresponds to a respective range of health scores.

Embodiment 20 is a system comprising one or more computers and one or more storage devices storing instructions that are operable, when executed by the one or more computers, to cause the one or more computers to perform the method of any one of embodiments 1-19.

Embodiment 21 is a computer storage medium encoded with a computer program, the program comprising instructions that are operable, when executed by data processing apparatus, to cause the data processing apparatus to perform the method of any one of embodiments 1-19.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain some cases, multitasking and parallel processing may be advantageous.

What is claimed is:

1. A method comprising:
    obtaining, by one or more processing devices, brain data captured by one or more brain imaging devices characterizing a brain of a patient, wherein the brain data comprises, for each of a plurality of pairs of parcellations formed from a set of parcellations in the brain of the patient where each pair comprises a first parcellation and a second parcellation, data characterizing a number of tracts connecting the first parcellation and the second parcellation, the set of parcellations comprising at least 100 parcellations;
    determining, by the one or more processing devices and from the brain data, a network graph comprising a plurality of nodes, wherein:
        one or more nodes of the plurality of nodes of the network graph corresponds to respective parcellations in the brain of the patient, and
        at least a first subset of the plurality of nodes of the network graph corresponds to a particular functional area of the brain, wherein the particular functional area of the brain comprises a plurality of parcellations from the set of parcellations;
    providing, by the one or more processing devices, data characterizing the network graph for display on a user device;
    generating, for at least a second subset of the plurality of nodes in the network graph, a measure of centrality of the node;
    generating, for the particular functional area of the brain and using the generated measures of centrality, a health score representing a measure of health of the particular functional area of the brain;
    generating a mental health prediction for the patient using the health score; and
    providing, for display on the user device, data characterizing the mental health prediction.

2. The method of claim 1, wherein:
    an edge between a first node and a second node of the network graph characterizes a connection between a parcellation corresponding to the first node and a parcellation corresponding to the second node, and
    determining a network graph from the brain data comprises, for the edge between the first node and the second node of the network graph, generating an edge weight according to the number of tracts connecting the parcellation corresponding to the first node and the parcellation corresponding to the second node.

3. The method of claim 2, wherein the edge weight for the edge between the first node and the second node in the network graph is generated according to one or more of i) the number of tracts connecting the parcellation corresponding to the first node and the parcellation corresponding to the second node, or ii) a measure of health of the tracts connecting the parcellation corresponding to the first node and the parcellation corresponding to the second node.

4. The method of claim 3, wherein the edge weight for the edge between the first node and the second node is a machine-learned linear combination of i) the number of tracts connecting the parcellation corresponding to the first node and the parcellation corresponding to the second node and ii) the measure of health of the tracts connecting the parcellation corresponding to the first node and the parcellation corresponding to the second node.

5. The method of claim 1, wherein the network graph includes a respective first subset of nodes corresponding to each of a plurality of different functional areas of the brain, and wherein the method further comprises generating, for each of the plurality of different functional areas of the brain and using the generated measures of centrality, a respective health score representing a measure of health of the functional areas of the brain.

6. The method of claim 5, wherein generating a mental health prediction for the patient comprises determining a relationship between the respective measures of health of the plurality of different functional areas of the brain.

7. The method of claim 1, wherein generating a health score for the particular functional area comprises generating the health score using i) the generated measures of centrality, ii) the number of tracts connecting each pair of parcellations in the particular functional area of the brain, and iii) a measure of health of the tracts connecting each pair of parcellations in the particular functional area of the brain.

8. The method of claim 7, wherein the health score for the particular functional area of the brain is a machine-learned linear combination of i) the generated measures of centrality, ii) the number of tracts connecting each pair of parcellations in the particular functional area of the brain, and iii) a measure of health of the tracts connecting each pair of parcellations in the particular functional area of the brain.

9. The method of claim 1, wherein generating a mental health prediction for the patient comprises generating a prediction of whether the patient has a particular brain disease.

10. The method of claim 9, wherein the particular brain disease is associated with a range of possible health of scores of the particular functional area of the brain.

11. The method of claim 10, wherein the range of possible health scores associated with the particular brain disease is machine learned, the learning comprising processing a plurality of training examples corresponding to respective other patients.

12. The method of claim 1, wherein:
    the obtained brain data corresponds to a first time point;
    the health score is a first health score that represents a measure of health of the functional area of the brain at the first time point;
    the method further comprises:
        obtaining second brain data corresponding to a second time point, and
        generating, for the particular functional area of the brain, a second health score representing a measure of health of the functional area of the brain at the second time point; and
    generating a mental health prediction for the patient comprises determining a change between the first health score and the second health score.

13. The method of claim 12, wherein:
    the first time point is a time point before a treatment was provided to the patient, and
    the second time point is a time point after the treatment was provided to the patient.

14. The method of claim 13, wherein the treatment provided to the patient included one or more of:
    a drug therapy;
    radiation therapy;
    magnetic therapy;
    light therapy;
    ultrasonic therapy;
    gene-modifying therapy;
    a surgery;
    physical therapy; or
    mental exercises.

15. The method of claim 13, wherein the mental health prediction comprises one or more of:
a measure of efficacy of the treatment; or
a performance measure of one or more entities that administered the treatment.

16. The method of claim 1, wherein generating a mental health prediction for the patient comprises determining a sequence of recommended treatments, wherein each recommended treatment in the sequence of recommended treatments corresponds to a respective range of health scores.

17. A system comprising one or more computers and one or more storage devices storing instructions that are operable, when executed by the one or more computers, to cause the one or more computers to perform operations comprising:
obtaining, by one or more processing devices, brain data captured by one or more brain imaging devices characterizing a brain of a patient, wherein the brain data comprises, for each of a plurality of pairs of parcellations formed from a set of parcellations in the brain of the patient where each pair comprises a first parcellation and a second parcellation, data characterizing a number of tracts connecting the first parcellation and the second parcellation, the set of parcellations comprising at least 100 parcellations;
determining, by the one or more processing devices and from the brain data, a network graph comprising a plurality of nodes, wherein:
one or more nodes of the plurality of nodes of the network graph corresponds to respective parcellations in the brain of the patient, and
at least a first subset of the plurality of nodes of the network graph corresponds to a particular functional area of the brain, wherein the particular functional area of the brain comprises a plurality of parcellations from the set of parcellations;
providing, by the one or more processing devices, data characterizing the network graph for display on a user device;
generating, for at least a second subset of the plurality of nodes in the network graph, a measure of centrality of the node;
generating, for the particular functional area of the brain and using the generated measures of centrality, a health score representing a measure of health of the particular functional area of the brain;
generating a mental health prediction for the patient using the health score; and
providing, for display on the user device, data characterizing the mental health prediction.

18. One or more non-transitory storage media storing instructions that when executed by one or more computers cause the one or more computers to perform operations comprising:
obtaining, by one or more processing devices, brain data captured by one or more brain imaging devices characterizing a brain of a patient, wherein the brain data comprises, for each of a plurality of pairs of parcellations formed from a set of parcellations in the brain of the patient where each pair comprises a first parcellation and a second parcellation, data characterizing a number of tracts connecting the first parcellation and the second parcellation, the set of parcellations comprising at least 100 parcellations;
determining, by the one or more processing devices and from the brain data, a network graph comprising a plurality of nodes, wherein:
one or more nodes of the plurality of nodes of the network graph corresponds to respective parcellations in the brain of the patient, and
at least a first subset of the plurality of nodes of the network graph corresponds to a particular functional area of the brain, wherein the particular functional area of the brain comprises a plurality of parcellations from the set of parcellations;
providing, by the one or more processing devices, data characterizing the network graph for display on a user device;
generating, for at least a second subset of the plurality of nodes in the network graph, a measure of centrality of the node;
generating, for the particular functional area of the brain and using the generated measures of centrality, a health score representing a measure of health of the particular functional area of the brain;
generating a mental health prediction for the patient using the health score; and
providing, for display on the user device, data characterizing the mental health prediction.

19. The method of claim 1, wherein generating a mental health prediction for the patient comprises determining a recommended treatment to provide to the patient.

20. The method of claim 19, wherein the recommended treatment is associated with a range of possible health of scores of the subset of parcellations.

21. The method of claim 20, wherein the range of possible health scores associated with the recommended treatment is machine learned, the learning comprising processing a plurality of training examples corresponding to respective other patients.

* * * * *